(12) United States Patent
Foster et al.

(10) Patent No.: US 7,446,184 B2
(45) Date of Patent: Nov. 4, 2008

(54) MAGENTA DYES AND THEIR USE IN INK-JET PRINTING

(75) Inventors: Clive Edwin Foster, Manchester (GB); David Schofield, Manchester (GB); Julie Ann Downey, Manchester (GB); Neil Burnham, Manchester (GB); Philip John Double, Manchester (GB); Roy Bradbury, Manchester (GB)

(73) Assignee: Fujifilm Imaging Colorants Limited, Manchester (GB)

( * ) Notice: Subject to any disclaimer, the term of this patent is extended or adjusted under 35 U.S.C. 154(b) by 0 days.

(21) Appl. No.: 10/583,272

(22) PCT Filed: Dec. 6, 2004

(86) PCT No.: PCT/GB2004/005125

§ 371 (c)(1),
(2), (4) Date: Mar. 2, 2007

(87) PCT Pub. No.: WO2005/058807

PCT Pub. Date: Jun. 30, 2005

(65) Prior Publication Data

US 2007/0276132 A1 Nov. 29, 2007

(30) Foreign Application Priority Data

Dec. 18, 2003 (GB) .................................. 0329247.1

(51) Int. Cl.
*C09B 31/072* (2006.01)
*C09B 62/09* (2006.01)
*C09D 11/02* (2006.01)

(52) U.S. Cl. .................... 534/797; 534/837; 106/31.48; 106/31.52; 347/86

(58) Field of Classification Search ................. 534/797, 534/837
See application file for complete search history.

(56) References Cited

U.S. PATENT DOCUMENTS

| 3,755,290 A | * | 8/1973 | De Montmollin et al. ... 534/643 |
|---|---|---|---|
| 5,075,428 A | | 12/1991 | Jaeger et al. |
| 5,359,042 A | | 10/1994 | Jaeger et al. |
| 5,599,386 A | | 2/1997 | Sano et al. |
| 5,756,693 A | | 5/1998 | Kenyon et al. |
| 5,759,247 A | | 6/1998 | Gregory et al. |
| 5,824,785 A | | 10/1998 | Baettig et al. |
| 5,883,234 A | | 3/1999 | Mennicke et al. |
| 6,190,423 B1 | | 2/2001 | Schumacher et al. |

FOREIGN PATENT DOCUMENTS

| EP | 0 406 629 A | 1/1991 |
|---|---|---|
| WO | WO 97/27250 A | 7/1997 |
| WO | WO 98/20077 A | 5/1998 |

* cited by examiner

*Primary Examiner*—Fiona T Powers
(74) *Attorney, Agent, or Firm*—Morgan, Lewis & Bockius LLP

(57) ABSTRACT

A compound of Formula (1) and salts thereof:

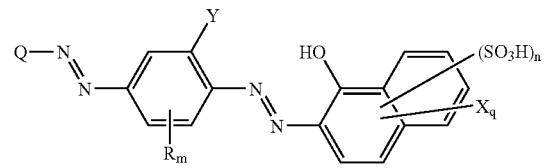

Formula (1)

wherein:
Q is an optionally substituted aryl ring;
Y is $CO_2H$, $SO_3H$ or $PO_3H_2$;
R and X are substituents;
m is 0 to 3;
n is 0 to 6; and
q is 0 to 6.

Also compositions comprising these compounds, ink-jet inks, an ink jet process and an ink-jet cartridge.

14 Claims, No Drawings

MAGENTA DYES AND THEIR USE IN INK-JET PRINTING

This invention relates to compounds suitable for use as dyes, to inks, to printing processes, to printed substrates and to ink-jet printer cartridges.

Ink-jet printing is a non-impact printing technique in which droplets of ink are ejected through a fine nozzle onto a substrate without bringing the nozzle into contact with the substrate. The set of inks used in this technique typically comprises yellow, magenta, cyan and black inks. The colour of the inks in any given ink-set is precisely matched so that when printed in combination they are able to reproduce a full colour spectrum.

While ink-jet printers have many advantages over other forms of printing and image development there are still technical challenges to be addressed. For example, there are the contradictory requirements of providing ink colorants that are soluble in the, usually aqueous, ink medium and yet do not run or smudge excessively when printed on paper. The inks need to dry quickly to avoid sheets sticking together after they have been printed, but they should not form a crust over the tiny nozzle used in the printer. Storage stability is also important to avoid particle formation that could block the tiny nozzles used in the printer. Furthermore, the resultant images desirably do not fade rapidly on exposure to light or common oxidising gases such as ozone.

With the advent of high-resolution digital cameras it is becoming increasingly common to use ink jet printers to print photographs. This avoids the expense of conventional silver halide photography and provides a print quickly. However, consumers expect that the print so produced will not fade or change colour with time and the colorants currently used in ink-jet printing fail to give an equivalent performance to silver halide photography.

The present invention provides a compound of Formula (1) and salts thereof:

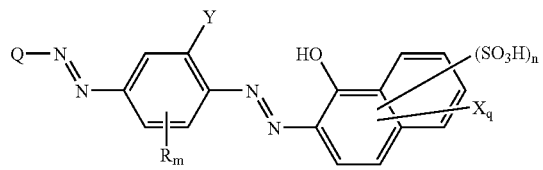

Formula (1)

wherein:
Q is an optionally substituted aryl ring;
Y is $CO_2H$, $SO_3H$ or $PO_3H_2$;
R and X are substituents;
m is 0 to 3;
n is 0 to 6; and
q is 0 to 6.

Preferably Q is optionally substituted naphthyl or optionally substituted phenyl, more preferably Q is optionally substituted phenyl.

R, X and optional substituents on Q are preferably independently selected from: optionally substituted alkyl (preferably $C_{1-4}$-alkyl), optionally substituted alkenyl (preferably $C_{1-4}$-alkenyl), optionally substituted alkynyl (preferably $C_{1-4}$-alkynyl), optionally substituted alkoxy (preferably $C_{1-4}$-alkoxy), optionally substituted aryl (preferably phenyl), optionally substituted aryloxy (preferably phenoxy), optionally substituted heterocyclyl (preferably triazinyl), polyalkylene oxide (preferably polyethylene oxide or polypropylene oxide), $CO_2H$, $SO_3H$, $PO_3H_2$, nitro, cyano, halo (preferably Cl and Br), ureido, $-SO_2F$, hydroxy, ester, $-NR^aR^b$, $-COR^a$, $-CONR^aR^b$, $-NHCOR^a$, carboxyester, sulfone, and $-SO_2NR^aR^b$ wherein $R^a$ and $R^b$ are each independently H or optionally substituted alkyl (especially $C_{1-4}$-alkyl). Optional substituents for any of the above substituents may be selected from the same list of substituents.

It is particularly preferred that Q is phenyl bearing at least one $CO_2H$, $SO_3H$ or $PO_3H_2$ substituent and optionally other substituents.

It is especially preferred that Q is phenyl with 1 or 2 substituents independently selected from the group consisting of $CO_2H$, $SO_3H$ or $PO_3H_2$.

Preferably m is 0.
Preferably n is 0 to 3, more preferably n is 1 to 3.
Preferably q is 0, 1 or 2.
In a first preferred embodiment n is 1, 2 or 3, more preferably 2 or 3, m is 0 and q is 0, 1 or 2.

Preferred compounds of Formula (1) in the first preferred embodiment are of Formula (2) and salts thereof:

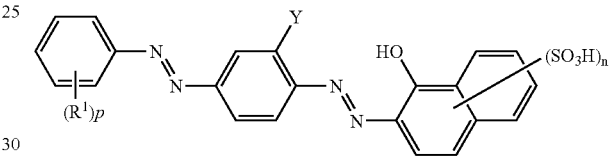

Formula (2)

wherein:
Y and $R^1$ independently are $CO_2H$, $SO_3H$ or $PO_3H_2$;
p is 1 or 2; and
n is 1 to 3.

Particularly preferred compounds of Formula (2) in the first preferred embodiment are of Formula (3) and Formula (4) and salts thereof:

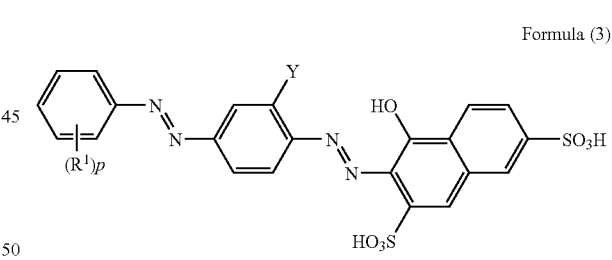

Formula (3)

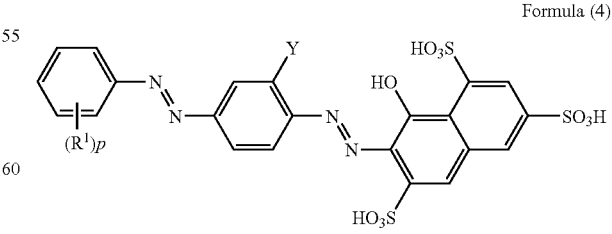

Formula (4)

wherein
Y and $R^1$ independently are $CO_2H$, $SO_3H$ or $PO_3H_2$; and
p is 1 or 2.

In the compounds of Formula (3) and (4) Y and $R^1$ are preferably independently $CO_2H$ or $SO_3H$.

In a second preferred embodiment n is 1, 2 or 3, more preferably 2, m is 0, q is 1 to 3 and X is Cl, Br, Fl or CN.

Preferred compounds of Formula (1) in the second preferred embodiment are of Formula (5) and salts thereof;

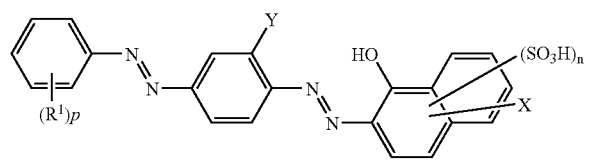

Formula (5)

wherein:
Y and $R^1$ independently are $CO_2H$, $SO_3H$ or $PO_3H_2$;
X is Cl, Br, Fl or CN
p is 1 or 2; and
n is 1 to 3.

Particularly preferred compounds of Formula (1) in the second preferred embodiment are of Formula (6) and Formula (7) and salts thereof:

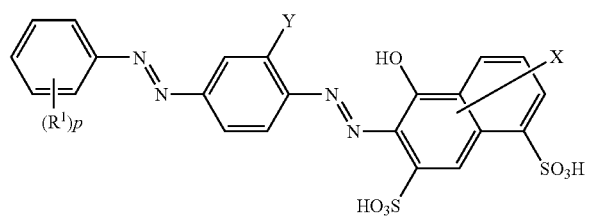

Formula (6)

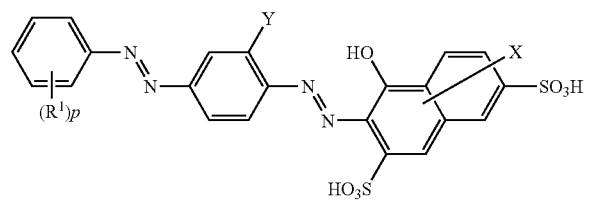

Formula (7)

wherein
Y and $R^1$ independently are $CO_2H$, $SO_3H$ or $PO_3H_2$;
X is Cl, Br or CN;
p is 1 or 2.

In a third preferred embodiment n is 0, m is 0, q is 1 or 2 and X is optionally substituted heterocyclyl, preferably optionally substituted triazyl.

The optional substituents on X when it is a heterocyclic ring may be selected from the list of preferred optional substituents given above. Preferably any optional substituent is hydroxyl.

Preferred compounds of Formula (1) in the third preferred embodiment are of Formula (8) and salts thereof;

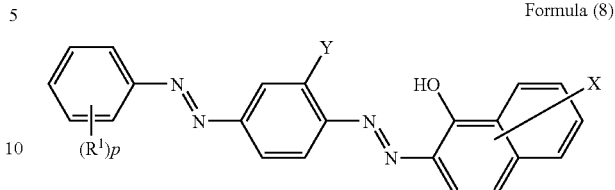

Formula (8)

wherein:
Y and $R^1$ independently are $CO_2H$, $SO_3H$ or $PO_3H_2$;
X is optionally substituted heterocyclyl; and
p is 1 or 2.

Particularly preferred compounds of Formula (1) in the second preferred embodiment are of Formula (9) and salts thereof:

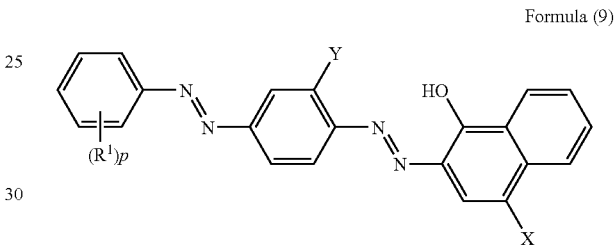

Formula (9)

wherein
Y and $R^1$ independently are $CO_2H$, $SO_3H$ or $PO_3H_2$;
X is optionally substituted triazinyl; and
p is 1 or 2.

It is especially preferred that in compounds of the third preferred embodiment that X is a group of formula:

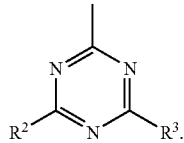

wherein $R^2$ and $R^3$ are substituents. $R^2$ and $R^3$ may be independently selected from the list given above of preferred substituents for R, X and optional substituents on Q. Preferably $R^2$ and $R^3$ are the same, more preferably $R^2$ and $R^3$ are both —OH.

The compounds of Formula (1) are also preferably free from fibre reactive groups. The term fibre reactive group is well known in the art and is described, for example, in EP 0356014 A1. Fibre reactive groups are capable, under suitable conditions, of reacting with the hydroxyl groups present in cellulosic fibres or with the amino groups present in natural fibres to form a covalent linkage between the fibre and the dye. As examples of fibre reactive groups excluded from the compounds of Formulae (1) there may be mentioned aliphatic sulfonyl groups which contain a sulfate ester group in beta-position to the sulfur atom, e.g. beta-sulfato-ethylsulfonyl groups, alpha, beta-unsaturated acyl radicals of aliphatic carboxylic acids, for example acrylic acid, alpha-chloro-acrylic acid, alpha-bromoacrylic acid, propiolic acid, maleic acid and mono- and dichloro maleic; also the acyl radicals of acids which contain a substituent which reacts with cellulose in the presence of an alkali, e.g. the radical of a halogenated aliphatic acid such as chloroacetic acid, beta-chloro and beta-bromopropionic acids and alpha, beta-dichloro- and dibromopropionic acids or radicals of vinylsulfonyl- or beta-chloroethylsulfonyl- or beta-sulfatoethyl-sulfonyl-endomethylene cyclohexane carboxylic acids. Other examples of cellulose reactive groups are tetrafluorocyclobutyl carbonyl, trifluoro-cyclobutenyl carbonyl, tetrafluorocyclobutylethenyl carbonyl, trifluoro-cyclobutenylethenyl carbonyl; activated halogenated 1,3-dicyanobenzene radicals; and heterocyclic radicals which contain 1, 2 or 3 nitrogen atoms in the heterocyclic ring and at least one cellulose reactive substituent on a carbon atom of the ring.

Many of the compounds described above may exist in the form of a salt. These salts are included within the scope of the present inventions.

The compounds described above may be converted to the salt form using known techniques.

Preferred salts are alkali metal salts, especially lithium, sodium and potassium, ammonium or a substituted ammonium salt (including a quaternary ammonium salt such as $((CH_3)_4N^+)$ or a mixture thereof. Especially preferred are salts with sodium, lithium, ammonia and volatile amines, more especially sodium salts.

The compounds described herein may exist in tautomeric forms other than those shown in this specification. These tautomers are also included within the scope of the present inventions.

The compounds described herein may also form metal complexes and these complexes are also included within the scope of the present inventions.

The metal in the metal complex is preferably a transition metal and more preferably is selected from nickel, cobalt, copper, zinc and chromium, particularly $Ni^{2+}$.

Metal complexes of the compounds described in this invention are preferably 1:1, 2:2 or 2:1, compound to metal. When the complex comprises more than one compound according to the present then the compound may be the same or different.

The metal complexes may also comprise 1 or more additional ligands. These ligands may be coloured or colourless and when there is more than 1 additional ligand they may be the same or different.

The compounds of the invention may be prepared using conventional techniques for the preparation of azo dyes, these methods are summarised in "Organic Chemistry in Colour"; Gordon, P. F. and Gregory, P; Springer-Verlag; pp 57-63: which is incorporated herein by reference.

For example, a compound of Formula (1) may be prepared by diazotising an amine of Formula (10):

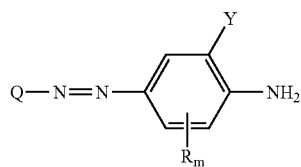

Formula (10)

wherein:
Q is an optionally substituted aryl ring;
Y is $CO_2H$, $SO_3H$ or $PO_3H_2$;
R is a substituent; and
m is 0 to 3: and coupling the resultant diazonium salt with a an optionally substituted naphth-1-ol.

Some monoazo compounds of Formula (10) are commercially available dyes, for example C.I. Acid Yellow 9. Others may be prepared by diazotising an amine of Formula (11):

Q-NH  Formula (11)

and coupling the resultant diazonium salt with a compound of Formula (12)

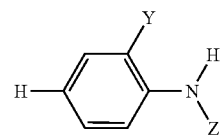

Formula (12)

wherein: Y is $CO_2H$, $SO_3H$ or $PO_3H_2$; and
Z is a protecting group, preferably methylene sulfonic acid.

Diazotisation is preferably performed at a temperature below 6° C., more preferably at a temperature in the range −10° C. to 5° C. Preferably diazotisation is performed in water, preferably at a pH below 7. Dilute mineral acid, e.g. HCl or $H_2SO_4$, may be used to achieve the desired acidic conditions. The subsequent coupling is preferably performed at a pH below 7 for the monazo intermediate and above pH 7 to form compounds of Formula (1).

The compounds of Formula (1), and salts and metal complexes thereof, have attractive, strong red, scarlet, magenta and violet shades and are valuable dyes for use in the preparation of ink-jet printing inks, especially magenta ink-jet printing inks. They benefit from a good balance of solubility, storage stability and fastness to water and light. In particular they display excellent light and ozone fastness.

According to a second aspect of the present invention there is provided a composition comprising a compound according to the first aspect of the invention and a liquid medium.

Preferred compositions comprise:
(a) from 0.01 to 30 parts of a compound according to the first aspect of the invention; and
(b) from 70 to 99.99 parts of a liquid medium; wherein all parts are by weight.

Preferably the number of parts of (a)+(b)=100.

The number of parts of component (a) is preferably from 0.1 to 20, more preferably from 0.5 to 15, and especially from 1 to 5 parts. The number of parts of component (b) is preferably from 99.9 to 80, more preferably from 99.5 to 85, especially from 99 to 95 parts.

Preferably component (a) is completely dissolved in component (b). Preferably component (a) has a solubility in component (b) at 20° C. of at least 10%. This allows the preparation of liquid dye concentrates that may be used to prepare more dilute inks and reduces the chance of the dye precipitating if evaporation of the liquid medium occurs during storage.

Preferred liquid media include water, a mixture of water and organic solvent and organic solvent free from water.

When the medium comprises a mixture of water and organic solvent, the weight ratio of water to organic solvent is preferably from 99:1 to 1:99, more preferably from 99:1 to 50:50 and especially from 95:5 to 80:20.

It is preferred that the organic solvent present in the mixture of water and organic solvent is a water-miscible organic solvent or a mixture of such solvents. Preferred water-miscible organic solvents include $C_{1-6}$-alkanols, preferably methanol, ethanol, n-propanol, isopropanol, n-butanol, sec-butanol, tert-butanol, n-pentanol, cyclopentanol and cyclohexanol; linear amides, preferably dimethylformamide or dimethylacetamide; ketones and ketone-alcohols, preferably acetone, methyl ether ketone, cyclohexanone and diacetone alcohol; water-miscible ethers, preferably tetrahydrofuran and dioxane; diols, preferably diols having from 2 to 12 carbon atoms, for example pentane-1,5-diol, ethylene glycol, propylene glycol, butylene glycol, pentylene glycol, hexylene glycol and thiodiglycol and oligo- and poly-alkyleneglycols, preferably diethylene glycol, triethylene glycol, polyethylene glycol and polypropylene glycol; triols, preferably glycerol and 1,2,6-hexanetriol; mono-$C_{1-4}$-alkyl ethers of diols, preferably mono-$C_{1-4}$-alkyl ethers of diols having 2 to 12 carbon atoms, especially 2-methoxyethanol, 2-(2-methoxyethoxy)ethanol, 2-(2-ethoxyethoxy)-ethanol, 2-[2-(2-methoxyethoxy)ethoxy]ethanol, 2-[2-(2-ethoxyethoxy)-ethoxy]-ethanol and ethyleneglycol monoallylether; cyclic amides, preferably 2-pyrrolidone, N-methyl-2-pyrrolidone, N-ethyl-2-pyrrolidone, caprolactam and 1,3-dimethylimidazolidone; cyclic esters, preferably caprolactone; sulfoxides, preferably dimethyl sulfoxide and sulfolane. Preferably the liquid medium comprises water and 2 or more, especially from 2 to 8, water-miscible organic solvents.

Especially preferred water-miscible organic solvents are cyclic amides, especially 2-pyrrolidone, N-methyl-pyrrolidone and N-ethyl-pyrrolidone; diols, especially 1,5-pentane diol, ethyleneglycol, thiodiglycol, diethyleneglycol and triethyleneglycol; and mono-$C_{1-4}$-alkyl and $C_{1-4}$-alkyl ethers of diols, more preferably mono-$C_{1-4}$-alkyl ethers of diols having 2 to 12 carbon atoms, especially 2-methoxy-2-ethoxy-2-ethoxyethanol.

Examples of further suitable liquid media comprising a mixture of water and one or more organic solvents are described in U.S. Pat. No. 4,963,189, U.S. Pat. No. 4,703,113, U.S. Pat. No. 4,626,284 and EP 4,251,50A.

When the liquid medium comprises organic solvent free from water, (i.e. less than 1% water by weight) the solvent preferably has a boiling point of from 30° to 200° C., more preferably of from 40° to 150° C., especially from 50 to 125° C. The organic solvent may be water-immiscible, water-miscible or a mixture of such solvents. Preferred water-miscible organic solvents are any of the hereinbefore-described water-miscible organic solvents and mixtures thereof. Preferred water-immiscible solvents include, for example, aliphatic hydrocarbons; esters, preferably ethyl acetate; chlorinated hydrocarbons, preferably $CH_2Cl_2$; and ethers, preferably diethyl ether; and mixtures thereof.

When the liquid medium comprises a water-immiscible organic solvent, preferably a polar solvent is included because this enhances solubility of the compound in the liquid medium. Examples of polar solvents include $C_{1-4}$-alcohols.

In view of the foregoing preferences it is especially preferred that where the liquid medium is organic solvent free from water it comprises a ketone (especially methyl ethyl ketone) and/or an alcohol (especially a $C_{1-4}$-alkanol, more especially ethanol or propanol).

The organic solvent free from water may be a single organic solvent or a mixture of two or more organic solvents. It is preferred that when the medium is an organic solvent free from water it is a mixture of 2 to 5 different organic solvents. This allows a medium to be selected that gives good control over the drying characteristics and storage stability of the ink.

Liquid media comprising an organic solvent free from water are particularly useful where fast drying times are required and particularly when printing onto hydrophobic and non-absorbent substrates, for example plastics, metal and glass.

The liquid medium may also contain additional components conventionally used in ink-jet printing inks, for example viscosity and surface tension modifiers, corrosion inhibitors, biocides, kogation reducing additives and surfactants which may be ionic or non-ionic.

Although not usually necessary, further colorants may be added to the composition to modify the shade and performance properties. Examples of such colorants include C.I. Acid Red 52 and 289; C.I. Direct Yellow 86, 132, 142 and 173; C.I. Direct Blue 199, and 307; C.I. Food Black 2; C.I. Direct Black 168 and 195; and C.I. Acid Yellow 23. Addition of such further dyes can increase overall solubility leading to less kogation (nozzle blockage) for the resultant ink.

Preferably the composition according to the second aspect of the invention is an ink-jet printing ink or a liquid dye concentrate.

Concentrates are useful as a means for transporting colorant and so minimising costs associated with drying the dye or transporting excess liquid.

It is preferred that the composition according to the invention is ink suitable for use in an ink-jet printer. Ink suitable for use in an ink-jet printer is ink which is able to repeatedly fire through an ink-jet printing head without causing blockage of the fine nozzles.

Inks suitable for use in an ink-jet printer according to the second aspect of the invention are preferably prepared using high purity ingredients and/or by purifying the composition after it has been prepared. Suitable purification techniques are well known, e.g. ultrafiltration, reverse osmosis, ion exchange and combinations thereof (either before or after they are incorporated in a composition according to the present invention). This purification results in the removal of substantially all of the inorganic salts and by-products resulting from its synthesis. Such purification assists in the preparation of a low viscosity aqueous solution suitable for use in an ink-jet printer.

The inks may be incorporated in an ink-jet printer as a high concentration magenta ink, a low concentration magenta ink or both a high concentration and a low concentration ink. In the latter case this can lead to improvements in the resolution and quality of printed images. Thus the present invention also provides a composition (preferably ink suitable for use in an ink-jet printer) where component (a) is present in an amount of 2.5 to 7 parts, more preferably 2.5 to 5 parts (a high concentration ink) or component (a) is present in an amount of 0.5 to 2.4 parts, more preferably 0.5 to 1.5 parts (a low concentration ink).

An ink suitable for use in an ink-jet printer preferably has a viscosity of less than 20 cP, more preferably less than 10 cP, especially less than 5 cP, at 25° C.

An ink suitable for use in an ink-jet printer preferably has a surface tension in the range 20-65 dynes/cm, more preferably in the range 30-60 dynes/cm at 25° C.

An ink suitable for use in an ink-jet printer preferably contains less than 500 ppm, more preferably less than 250 ppm, especially less than 100 ppm, more especially less than 10 ppm in total of divalent and trivalent metal ions (other than any divalent and trivalent metal ions bound to a colorant of Formula (1) or any other component of the ink).

Preferably an ink suitable for use in an ink-jet printer has been filtered through a filter having a mean pore size below 10 μm, more preferably below 3 μm, especially below 2 μm, more especially below 1 μm. This filtration removes particulate matter that could otherwise block the fine nozzles found in many ink-jet printers.

Preferably an ink suitable for use in an ink-jet printer contains less than 500 ppm, more preferably less than 250 ppm, especially less than 100 ppm, more especially less than 10 ppm in total of halide ions.

A third aspect of the invention provides a process for forming an image on a substrate comprising applying a composition according to the second aspect of the invention thereto by means of an ink-jet printer.

The ink-jet printer preferably applies the composition to the substrate in the form of droplets that are ejected through a small orifice onto the substrate. Preferred ink-jet printers are piezoelectric ink-jet printers and thermal ink-jet printers. In thermal ink-jet printers, programmed pulses of heat are applied to the ink in a reservoir by means of a resistor adjacent to the orifice, thereby causing the ink to be ejected from the orifice in the form of small droplets directed towards the substrate during relative movement between the substrate and the orifice. In piezoelectric ink-jet printers the oscillation of a small crystal causes ejection of the ink from the orifice. Alternately the ink can be ejected by an electromechanical actuator connected to a moveable paddle or plunger, for example as described in International Patent Application WO 00/48938 and International Patent Application WO 00/55089.

The substrate is preferably paper, plastic, textile, metal or glass, more preferably paper, an overhead projector slide or a textile material, especially paper.

Preferred papers are plain, treated or coated papers which may have an acid, alkaline or neutral character.

It is especially preferred that the paper is a photographic quality ink-jet paper.

A fourth aspect of the present invention provides a substrate, preferably a paper, plastic, textile, metal or glass, more preferably paper, an overhead projector slide or a textile material, especially paper more especially plain, coated or treated papers, particularly photographic quality paper printed with a composition according to the second aspect of the invention, a compound according to the first aspect of the invention or by means of a process according to third aspect of the invention.

It is especially preferred that the printed substrate is a print of a photograph.

A fifth aspect of the present invention provides an ink-jet printer cartridge comprising a chamber and an ink wherein the ink is in the chamber and the ink is as defined in the second aspect of the present invention.

The invention is further illustrated by the following Examples in which all parts and percentages are by weight unless otherwise stated.

EXAMPLE 1

Preparation of

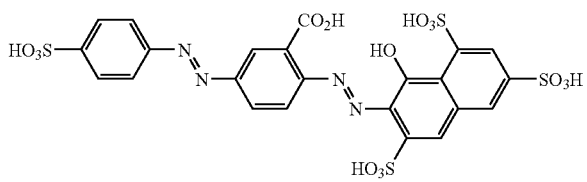

Stage 1

Preparation of 2-((sulfomethyl)amino)benzoic acid

Formaldehyde solution (37%, 31.6 g, 0.4 mol) and sodium bisulfite (38 g, 0.37 mol) were dissolved in water (200 ml) and the stirred mixture warmed to 60° C. Anthranilic acid (50 g, 0.37 mol) was dissolved in water (200 ml) at pH 7, and this solution was added to the bisulfite adduct solution, maintaining the temperature at 60-70° C. for 2 hours. The reaction mixture was allowed to cool slowly before hydrochloric acid was added to precipitate the product as a white solid. The product was collected by filtration and washed with saturated sodium chloride solution and then acetone. The dried product (34 g) contained 22.5% salt.

Stage 2

Preparation of 2-amino-5-((4-sulfophenyl)diazenyl)benzoic acid

Sulfanilic acid (8.65 g, 0.05 mol) and sodium nitrite (3.8 g) were dissolved in water (pH 8, 100 ml). This solution was added to a beaker containing ice (30 g) and concentrated hydrochloric acid (15 ml). After stirring for 15 minutes, sulfamic acid (0.5 g) was added. This diazonium salt solution was added to a solution of the 2-((sulfomethyl)amino)benzoic acid prepared in stage 1 in water (150 ml) at 0 to 5° C. The reaction mixture was stirred at 0-5° C. for 1.5 hours while the pH of the reaction medium was maintained at pH 4 to 4.5 by the addition of dilute sodium hydroxide solution. When the diazonium salt had been consumed the product was precipitated by the addition of 2M hydrochloric acid. The precipitate was collected by filtration and then dissolved in water (200 ml) adjusted to pH 12 with lithium hydroxide. The resultant solution was stirred at 70° C. for 2 hours, maintaining the pH by periodic addition of 2M lithium hydroxide solution. After cooling, the reaction mixture was adjusted to pH6 with 2M hydrochloric acid. The precipitated dye was collected by filtration as a brown solid (18 g).

Stage 3

Preparation of the Title Product

The monoazo dye from stage 2 (5.2 g, equivalent to 0.01 mol after correction for the salt content) and sodium nitrite (0.76 g, 0.011 mol) were dissolved in water (100 ml, pH 8) and poured into a beaker containing ice (30 g) and concentrated hydrochloric acid (8 ml) After 15 minutes, sulfamic acid (0.5 g) was added to the stirred solution. The diazonium suspension was then added to a beaker containing 8-hydroxynaphthalene-1,3,6-trisulfonic acid (7.5 g, 0.01 mol allowing for salt content) in 100 ml water, maintaining the pH at pH 9 to 10 throughout the addition. When all the diazonium salt had been consumed the pH was adjusted to pH 4 by the addition of concentrated hydrochloric acid. Salt, 20% w/v, was then added to initiate precipitation. The black solid that formed was collected by filtration, washed with brine and then acetone. The dried product (5 g) was reconstituted in water (100 ml) and dialysed to low conductivity.

EXAMPLE 2

Preparation of

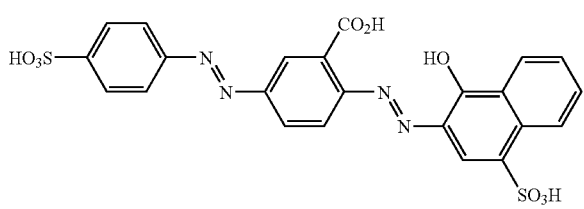

The compound of Example 2 was prepared as described in Example 1 except that in stage 3, 1-hydroxynaphthalene-4-sulfonic acid was used in place of 8-hydroxynaphthalene-1,3,6-trisulfonic acid.

EXAMPLE 3

Preparation of

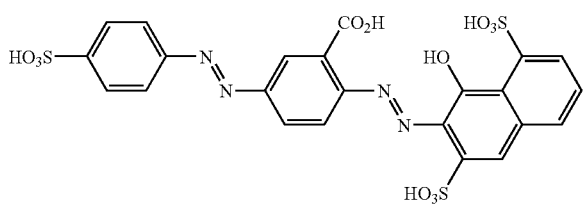

The compound of Example 3 was prepared as described in Example 1 except that in stage 3, 1-hydroxynaphthalene-3,8-disulfonic acid was used in place of 8-hydroxynaphthalene-1,3,6-trisulfonic acid.

EXAMPLE 4

Preparation of

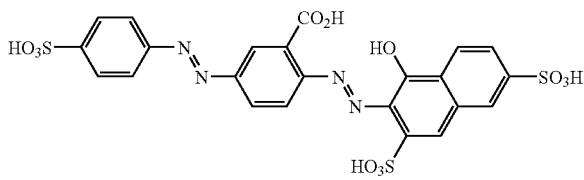

The compound of Example 4 was prepared as described in Example 1 except that in stage 3, 1-hydroxynaphthalene-3,6-disulfonic acid was used in place of 8-hydroxynaphthalene-1,3,6-trisulfonic acid.

EXAMPLE 5

Preparation of

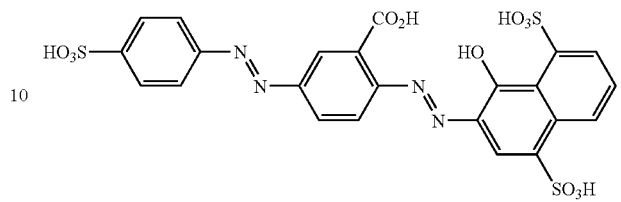

The compound of Example 5 was prepared as described in Example 1 except that in stage 3, 1-hydroxynaphthalene-4,8-disulfonic acid was used in place of 8-hydroxynaphthalene-1,3,6-trisulfonic acid.

EXAMPLE 6

Preparation of

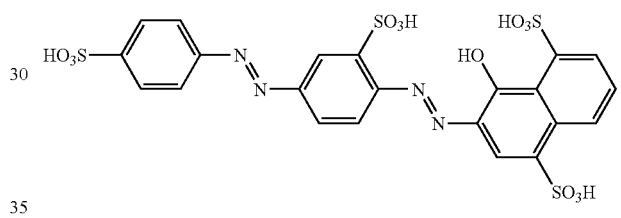

The compound of Example 6 was prepared as described in Example 1, stage 3 except that 4-amino-1,1'-azobenzene-3,4'-disulfonic acid (a compound commercially available from Aldrich Chemicals) was used in place of the product of Example 1, stage 2 and 1-hydroxynaphthalene-4,8-disulfonic acid was used in place of 8-hydroxynaphthalene-1,3,6-trisulfonic acid.

EXAMPLE 7

Preparation of

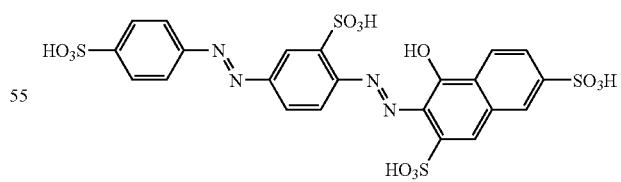

The compound of Example 7 was prepared as described in Example 1, stage 3 except that 4-amino-1,1'-azobenzene-3,4'-disulfonic acid (a compound commercially available from Aldrich Chemical) was used in place of the product of Example 1, stage 2 and 1-hydroxynaphthalene-3,6-disulfonic acid was used in place of 8-hydroxynaphthalene-1,3,6-trisulfonic acid.

EXAMPLE 8

Preparation of

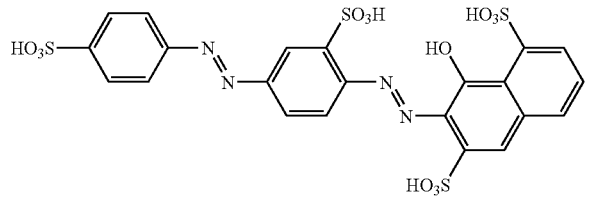

The compound of Example 8 was prepared as described in Example 1, stage 3 except that 4-amino-1,1'-azobenzene-3,4'-disulfonic acid (a compound commercially available from Aldrich Chemical) was used in place of the product of Example 1, stage 2 and 1-hydroxynaphthalene-3,8-disulfonic acid was used in place of 8-hydroxynaphthalene-1,3,6-trisulfonic acid.

EXAMPLE 9

Preparation of

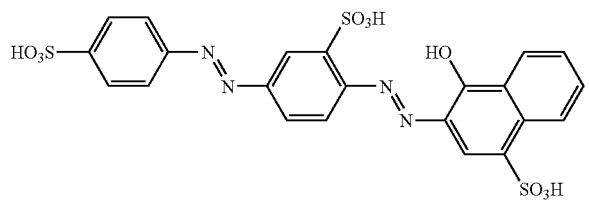

The compound of Example 9 was prepared as described in Example 1, stage 3 except that 4-amino-1,1'-azobenzene-3,4'-disulfonic acid (a compound commercially available from Aldrich Chemical) was used in place of the product of Example 1, stage 2 and 1-hydroxynaphthalene-4-sulfonic acid was used in place of 8-hydroxynaphthalene-1,3,6-trisulfonic acid.

EXAMPLE 10

Preparation of

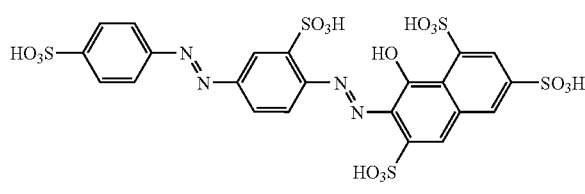

The compound of Example 10 was prepared as described in Example 1, stage 3 except that 4-amino-1,1'-azobenzene-3,4'-disulfonic acid (a compound commercially available from Aldrich Chemical) was used in place of the product of Example 1, stage 2.

EXAMPLE 11

Preparation of

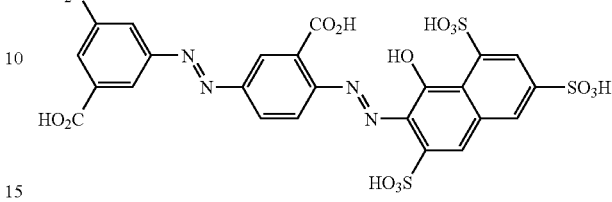

The compound of Example 11 was prepared as described in Example 1 except that in stage 2,5-aminobenzene-1,3-dicarboxylic acid was used in place of sulfanilic acid.

EXAMPLE 12

Preparation of

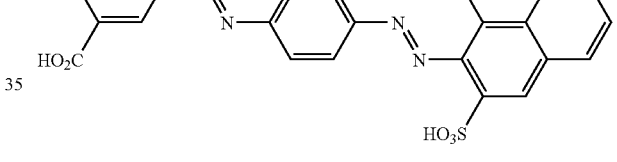

The compound of Example 12 was prepared as described in Example 1 except that in stage 2,5-aminobenzene-1,3-dicarboxylic acid was used in place of sulfanilic acid and in stage 3, 1-hydroxynaphthalene-3,8-disulfonic acid was used in place of 8-hydroxynaphthalene-1,3,6-trisulfonic acid.

EXAMPLE 13

Preparation of

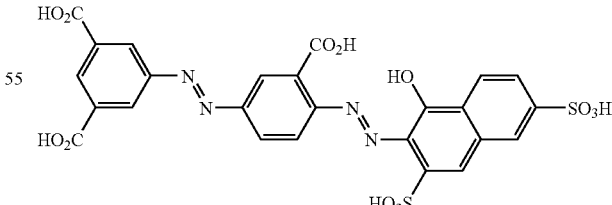

The compound of Example 13 was prepared as described in Example 1 except that in stage 2, 5-aminobenzene-1,3-dicarboxylic acid was used in place of sulfanilic acid and in stage 3, 1-hydroxynaphthalene-3,6-disulfonic acid was used in place of 8-hydroxynaphthalene-1,3,6-trisulfonic acid.

EXAMPLE 14

Preparation of

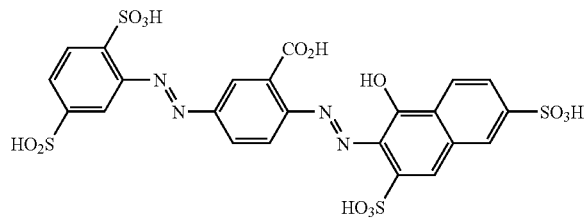

The compound of Example 14 was prepared as described in Example 1 except that in stage 2 1-aminobenzene-2,5-disulfonic acid was used in place of sulfanilic acid and in stage 3, 1-hydroxynaphthalene-3,6-disulfonic acid was used in place of 8-hydroxynaphthalene-1,3,6-trisulfonic acid.

EXAMPLE 15

Preparation of

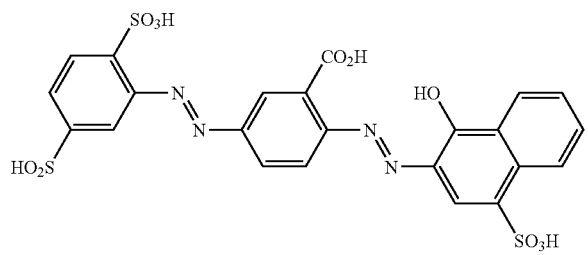

The compound of Example 15 was prepared as described in Example 1 except that in stage 2, 1-aminobenzene-2,5-disulfonic acid was used in place of sulfanilic acid and in stage 3, 1-hydroxynaphthalene-4-sulfonic acid was used in place of 8-hydroxynaphthalene-1,3,6-trisulfonic acid.

EXAMPLE 16

Preparation of

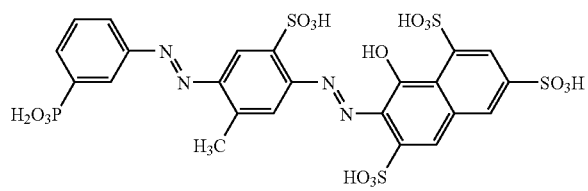

The compound of Example 16 was prepared as described in Example 1 except that in stage 2, 1-aminobenzene-3-phosphonic acid was used in place of sulfanilic acid and in stage 1, 2-amino-4-methyl-benzenesulfonic acid was used in place of anthranilic acid.

EXAMPLE 17

Preparation of

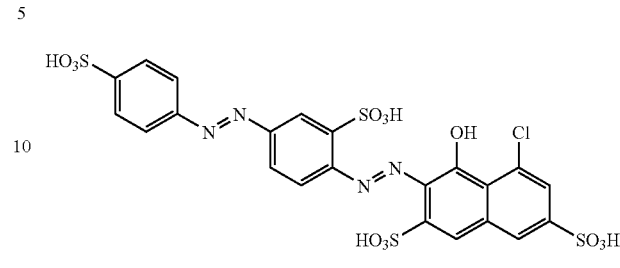

The compound of Example 17 was prepared as described in Example 1, stage 3 except that 4-amino-1,1'-azobenzene-3,4'-disulfonic acid, a compound commercially available from Aldrich Chemical, was used in place of the product of Example 1, stage 2 and 8-chloro-1-hydroxynaphthalene-3,6-disulfonic acid (prepared analogously to Example 31, stage 1) was used in place of 8-hydroxynaphthalene-1,3,6-trisulfonic acid. A solution of the dye in water had a λ max of 534 nm.

EXAMPLE 18

Preparation of

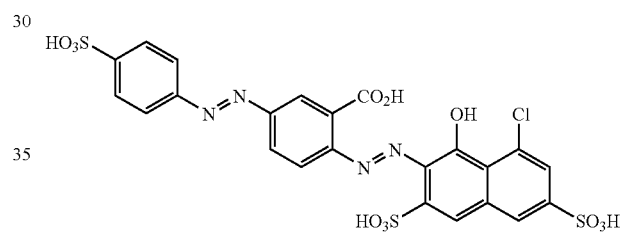

The compound of Example 18 was prepared as described in Example 1 except that in stage 3 8-chloro-1-hydroxynaphthalene-3,6-disulfonic acid (prepared analogously to example 31, stage 1) was used in place of 8-hydroxynaphthalene-1,3,6-trisulfonic acid. A solution of the dye in water had λ max at 528 and 546 nm.

EXAMPLE 19

Preparation of

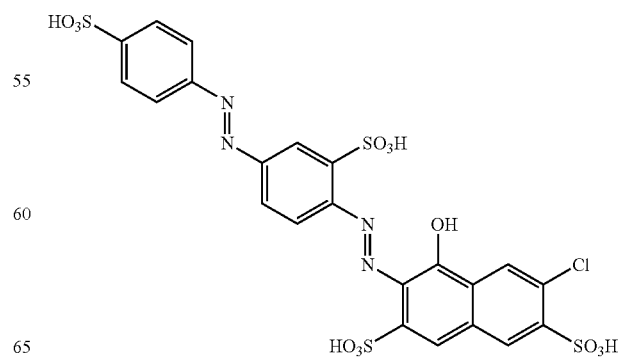

The compound of Example 19 was prepared as described in Example 1, stage 3 except that 3 4-amino-1,1'-azobenzene-3,4'-disulfonic acid, a compound commercially available from Aldrich Chemical, was used in place of the product of Example 1, stage 2 and 7-chloro-1-hydroxynaphthalene-3,6-disulfonic acid (prepared analogously to Example 31, stage 1) was used in place of 8-hydroxynaphthalene-1,3,6-trisulfonic acid. A solution of the dye in water had a λ max of 520 nm.

EXAMPLE 20

Preparation of

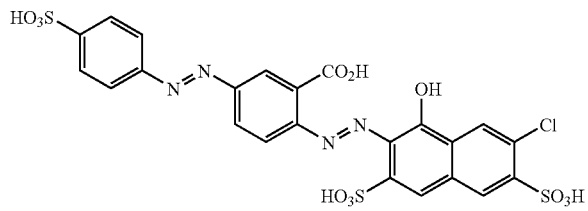

The compound of Example 20 was prepared as described in Example 1 except that in stage 3, 7-chloro-1-hydroxynaphthalene-3,6-disulfonic acid (prepared analogously to Example 31, stage 1) was used in place of 8-hydroxynaphthalene-1,3,6-trisulfonic acid. A solution of the dye in water had λ max of 528 and 546 nm.

EXAMPLE 21
Preparation of

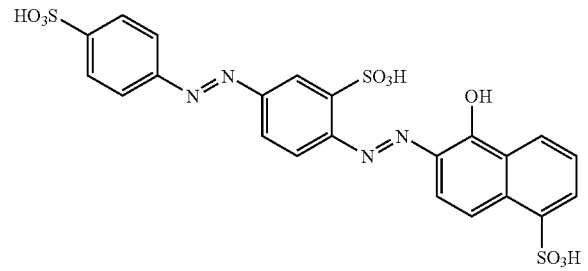

The compound of Example 21 was prepared as described in Example 1, stage 3 except that 4-amino-1,1'-azobenzene-3,4'-disulfonic acid, a compound commercially available from Aldrich Chemical, was used in place of the product of Example 1, stage 2 and 1-hydroxynaphthalene-5-sulfonic acid was used in place of 8-hydroxynaphthalene-1,3,6-trisulfonic acid. A solution of the dye in water had a λ max of 522 nm.

EXAMPLE 22
Preparation of

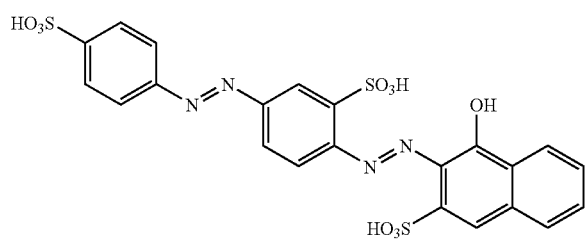

The compound of Example 22 was prepared as described in Example 1, stage 3 except that 4-amino-1,1'-azobenzene-3,4'-disulfonic acid, a compound commercially available from Aldrich Chemical, was used in place of the product of Example 1, stage 2 and 1-hydroxynaphthalene-3-sulfonic acid was used in place of 8-hydroxynaphthalene-1,3,6-trisulfonic acid. A solution of the dye in water had a λ max of 512 nm.

EXAMPLE 23
Preparation of

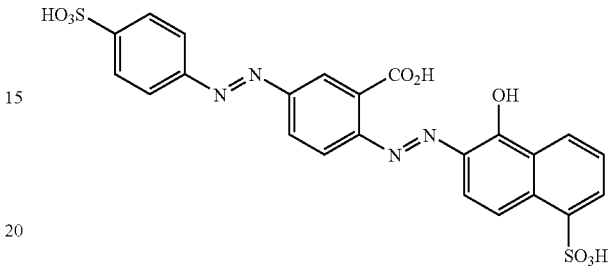

The compound of Example 23 was prepared as described in Example 1 except that in stage 3, 1-hydroxynaphthalene-5-sulfonic acid was used in place of 8-hydroxynaphthalene-1,3,6-trisulfonic acid. A solution of the dye in water had a λ max of 528 nm.

EXAMPLE 24
Preparation of

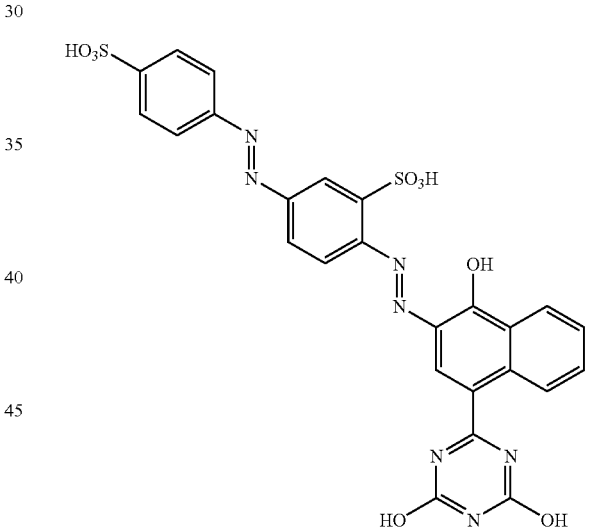

Stage 1    Preparation of
6-(4-hydroxy-1-naphthyl)-1,3,5-triazine-2,4-diol

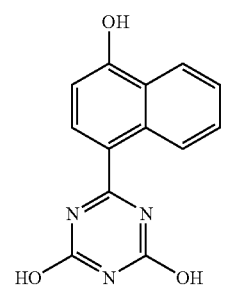

Cyanuric Chloride (64 g, 0.3468 mol) was dissolved in dry toluene (400 ml) then 1-naphthol (50 g, 0.347 mol) added slowly, followed by careful addition of powdered aluminium chloride (47.63 g, 0.352 mol) a thick brown-orange precipitate formed after a mild exotherm. The reaction mixture was stirred at room temperature for 1.5 hours, and then the precipitate was collected by filtration, and stirred in a mixture of water/ice (1000 ml) and concentrated hydrochloric acid (100 ml), then re-filtered. The resulting intermediate was dissolved in a mixture of water (500 ml) and concentrated sodium hydroxide (50 ml) and the stirred mixture warmed to 70° C. for 2 hours. The reaction mixture was allowed to cool slowly before hydrochloric acid was added to precipitate the product as an orange solid. The product was collected by filtration. The dried product (88 g) contained 16% salt.

Stage 2

Preparation of the Title Compound

The compound of Example 24 was prepared as described in Example 1, stage 3 except 4-amino-1,1'-azobenzene-3,4'-disulfonic acid, a compound commercially available from Aldrich Chemical, was used in place of the product of Example 1, stage 2 and the product of this Example, stage 1, was used in place of 8-hydroxynaphthalene-1,3,6-trisulfonic acid. A solution of the dye in water had a λ max of 526 nm.

EXAMPLE 25

Preparation of

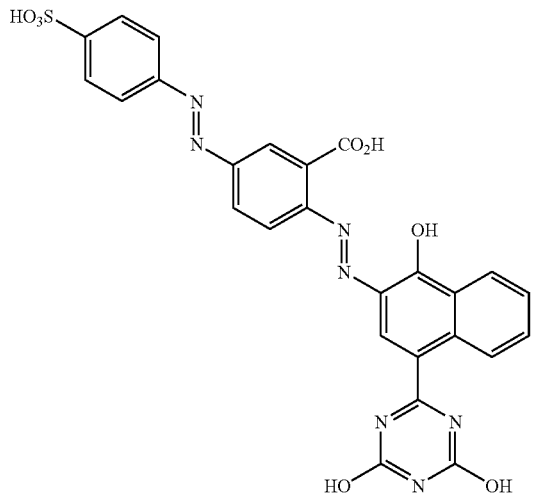

The compound of Example 25 was prepared as described in Example 1, stage 3, except the product of Example 24, stage 1, was used in place of 8-hydroxynaphthalene-1,3,6-trisulfonic acid. A solution of the dye in water had a λ max of 528 nm.

EXAMPLE 26

Preparation of

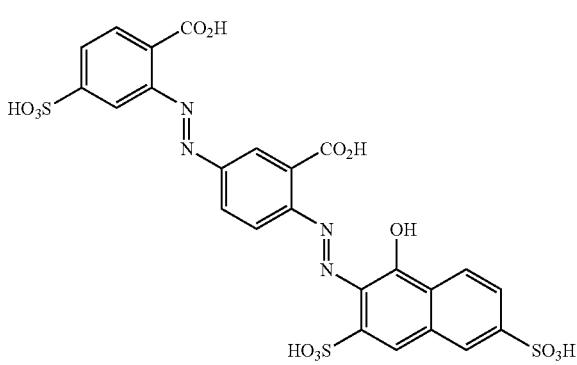

The compound of Example 26 was prepared as described in Example 1 except that in stage 2, 2-amino-4-sulfobenzoic acid was used in place of sulfanilic acid and in stage 3,1-hydroxynaphthalene-3,6-disulfonic acid was used in place of 8-hydroxynaphthalene-1,3,6-trisulfonic acid. A solution of the dye in water had a λ max of 536 nm.

EXAMPLE 27

Preparation of

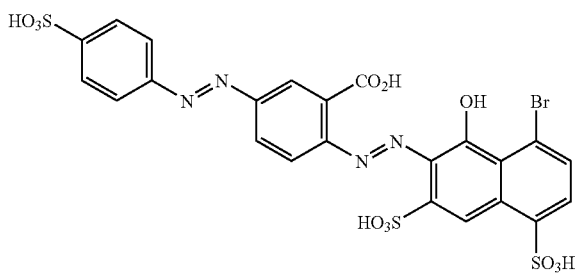

The compound of Example 27 was prepared as described in Example 1 except that in stage 3, 8-bromo-1-hydroxynaphthalene-3,5-disulfonic acid (prepared analogously to Example 31, stage 1) was used in place of 8-hydroxynaphthalene-1,3,6-trisulfonic acid. A solution of the dye in water had a λ max of 542 nm.

EXAMPLE 28

Preparation of

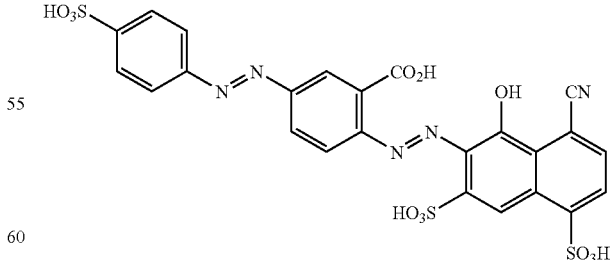

The compound of Example 28 was prepared as described in Example 1 except that in stage 3, 8-cyano-1-hydroxynaphthalene-3,5-disulfonic acid (prepared analogously to Example 32, stage 1) was used in place of 8-hydroxynaphthalene-1,3,6-trisulfonic acid. A solution of the dye in water had a λ max of 546 nm.

EXAMPLE 29

Preparation of

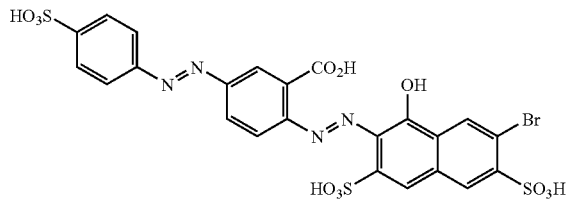

The compound of Example 29 was prepared as described in Example 1 except that in stage 3, 7-bromo-1-hydroxynaphthalene-3,6-disulfonic acid (prepared analogously to Example 31, stage 1) was used in place of 8-hydroxynaphthalene-1,3,6-trisulfonic acid. A solution of the dye in water had a λ max of 548 nm.

EXAMPLE 30

Preparation of

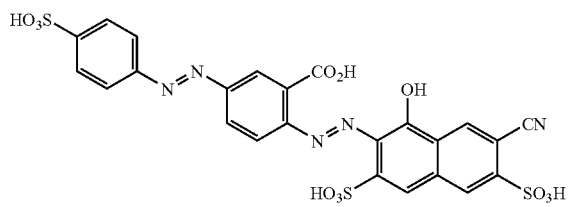

The compound of Example 30 was prepared as described in Example 1 except that in stage 3, 7-cyano-1-hydroxynaphthalene-3,6-disulfonic acid (prepared analogously to Example 32, stage 1) was used in place of 8-hydroxynaphthalene-1,3,6-trisulfonic acid. A solution of the dye in water had a λ max of 546 nm.

EXAMPLE 31

Preparation of

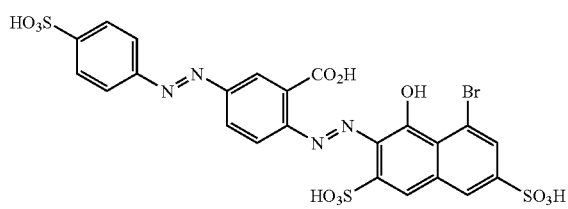

Stage 1

Preparation of 1-bromo-8-hydroxynaphthalene-3,6-disulfonic acid

1-Amino-8-hydroxynaphthalene-3,6-disulfonic acid (72% strength, 44.4 g, 0.1 mol) was stirred in a mixture of water (340 mls) and 48% hydrobromic acid (20 mls). The suspension was cooled to 0-5° C. and sodium nitrite (7.6 g, 0.11 mol) was added in small portions. The mixture was stirred for 2 hours at 0-5° C. and then the excess nitrous acid was destroyed by the addition of sulfamic acid solution. Further 48% hydrobromic acid (70 mls) was added and the mixture cooled to 5° C. A solution of copper (I) bromide (14.4 g, 0.1 mol) in 48% hydrobromic acid (30 mls) and water (20 mls) was then added dropwise at 0-5° C. The mixture was stirred for 10 minutes at 5° C. and then the temperature was slowly raised to and maintained at 90° C. for 1 hour. The reaction mixture was cooled to room temperature and sodium chloride added (30% w/v). The product was collected by filtration and washed with 20% sodium chloride solution. The dried product (56 g) contained 49% sodium chloride. Yield 74%.

Stage 2

Preparation of the Title Compound

The compound of Example 31 was prepared as described in Example 1 except that in stage 3, 8-bromo-1-hydroxynaphthalene-3,6-disulfonic acid (from Example 31, stage 1) was used in place of 8-hydroxynaphthalene-1,3,6-trisulfonic acid.

EXAMPLE 32

Preparation of

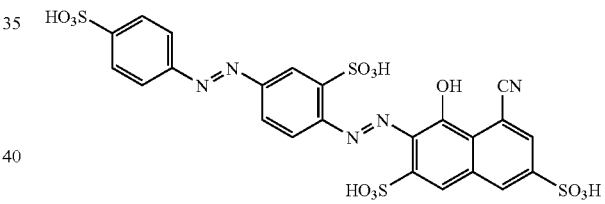

Stage 1

Preparation of 1-cyano-8-hydroxynaphthalene-3,6-disulfonic acid

1-Bromo-8-hydroxynaphthalene-3,6-disulfonic acid (51% strength, 15.0 g, 0.02 mol, prepared as in Example 31, stage 1) was stirred in N,N-dimethylformamide (100 mls). Copper (I) cyamide (2.0 g, 0.022 mol) was added and the mixture boiled under reflux until HPLC analysis indicated complete reaction. In this example 5 hours was required. If necessary further copper cyamide could be added during the reaction. The reaction mixture was cooled down and a small amount of insoluble material removed by filtration. The solvent was removed from the filtrate under vacuum to leave a brown tar. This was slurried in water and a small amount of solid removed by filtration. The filtrate was concentrated to 100 mls and the product precipitated by the addition of solid sodium chloride. The product was recovered by filtration, washed with brine and dried. The dried product (8.9 g) contained 50% sodium chloride. Yield 67%.

Stage 2
Preparation of the Title Compound

The compound of Example 32 was prepared as described in Example 1, stage 3, except 4-amino-1,1'-azobenzene-3,4'-disulfonic acid (a compound commercially available from Aldrich Chemical) was used in place of the product of Example 1, stage 2, and 8-cyano-1-hydroxynaphthalene-3,6-disulfonic acid, from Example 32 stage 1, was used in place of 8-hydroxynaphthalene-1,3,6-trisulfonic acid.

EXAMPLE 33
Preparation of

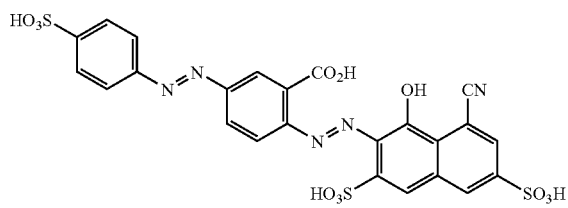

The compound of Example 33 was prepared as described in Example 1 except that in stage 3, 8-cyano-1-hydroxynaphthalene-3,6-disulfonic acid, prepared as in Example 32 stage 1, was used in place of 8-hydroxynaphthalene-1,3,6-trisulfonic acid. A solution of the dye in water had a λ max of 548 nm.

COMPARATIVE EXAMPLES

Comparative Example C1 was prepared as described in Example 1 of U.S. Pat. No. 5,599,386

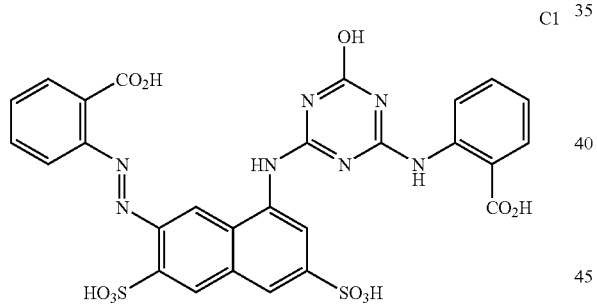

Comparative Example C2 was prepared as described for Dye 101 in U.S. Pat. No. 5,824,785.

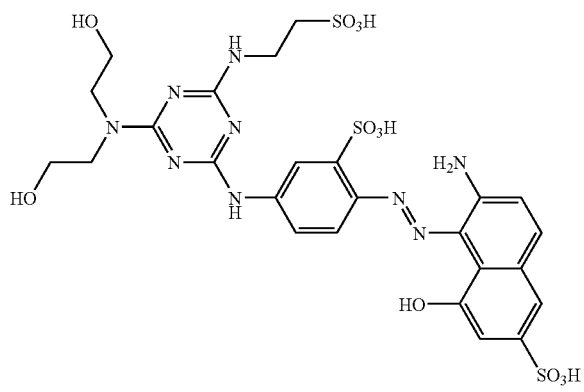

EXAMPLES 34 TO 47 INKS AND INK-JET PRINTING

Preparation of Inks

Inks were prepared from the comparative dyes and dyes of the Examples, as shown in Table 1, by dissolving 3 g of a dye in 97 ml of a liquid medium consisting of 5 parts 2-pyrrolidone; 5 parts thiodiethylene glycol; 1 part Surfynol™ 465 and 89 parts water and adjusting the pH to between pH 8 to 9 with sodium hydroxide. Surfynol™ 465 is a surfactant from Air Products. Inks such as this would have a viscosity of less than 20 cP at 25° C.; a surface tension in the range 20-65 dynes/cm at 25° C.; less than 500 ppm in total of divalent and trivalent metal ions (other than any divalent and trivalent metal ions bound to a colorant of Formula (1) or any other component of the ink); and less than 500 ppm in total of halide ions.

TABLE 1

| Dye of Example | Ink Example |
| --- | --- |
| 2 | 34 |
| 4 | 35 |
| 12 | 36 |
| 14 | 37 |
| 17 | 38 |
| 19 | 39 |
| 20 | 40 |
| 25 | 41 |
| 26 | 42 |
| 27 | 43 |
| 28 | 44 |
| 29 | 45 |
| 31 | 46 |
| 33 | 47 |
| Comparative Dye 1 | Ink C1 |
| Comparative Dye 2 | Ink C2 |

Ink-Jet Printing

Inks prepared as described above were filtered through a 0.45 micron nylon filter and then incorporated into empty print cartridges using a syringe.

These inks were then printed onto Epson™ Premium Glossy Photo Paper (SEC PM) and Canon™ Premium PR101 Photo Paper (PR101) using an ink-jet printer.

The prints so formed were tested for ozone fastness by exposure to 1 ppm ozone at 40° C., 50% relative humidity for 24 hrs in a Hampden 903 Ozone cabinet. Fastness of the printed ink to ozone is judged by the difference in the optical density before and after exposure to ozone.

Optical measurements were performed using a Gretag™ spectrolino spectrophotometer set to the following parameters:

| | |
|---|---|
| Measuring Geometry | 0°/45° |
| Spectral Range | 370-720 nm |
| Spectral Interval | 10 nm |
| Illuminant | D65 |
| Observer | 2° (CIE 1931) |
| Density | Ansi A |
| External Filler | None |

Ozone fastness was assessed by the percentage change in the optical density (OD) of the print, where a lower figure indicates higher fastness. Results are shown in Table 2.

TABLE 2

| Example | SEC PM % Change in OD | PR101 % Change in OD |
|---|---|---|
| 34 | 14 | 18 |
| 35 | 13 | 13 |
| 36 | 17 | 18 |
| 37 | 10 | 11 |
| 38 | 9 | 9 |
| 39 | 11 | 11 |
| 40 | 11 | 14 |
| 41 | 8 | 25 |
| 42 | 17 | 17 |
| 43 | 6 | 9 |
| 44 | 3 | 8 |
| 45 | 12 | 13 |
| 46 | 17 | 15 |
| 47 | 12 | 13 |

TABLE 2-continued

| Example | SEC PM % Change in OD | PR101 % Change in OD |
|---|---|---|
| Ink C1 | 24 | 23 |
| Ink C2 | 72 | 72 |

Table 2 shows that the inks of the present invention have a higher ozone fastness than the comparative dyes.

Further Inks

The inks described in Tables A and B may be prepared wherein the Dye described in the first column is the compound made in the above Example of the same number. Numbers quoted in the second column onwards refer to the number of parts of the relevant ingredient and all parts are by weight. The inks may be applied to paper by inkjet printing.

The following abbreviations are used in Tables A and B:

PG=propylene glycol
DEG=diethylene glycol
NMP=N-methylpyrollidone
DMK=dimethylketone
IPA=isopropanol
MeOH=methanol
2P=2-pyrrolidone
MIBK=methylisobutyl ketone
P12=propane-1,2-diol
BDL=butane-2,3-diol
CET=cetyl ammonium bromide
PHO=$Na_2HPO_4$ and
TBT=tertiary butanol
TDG=thiodiglycol

TABLE A

| Example | Dye Content | Water | PG | DEG | NMP | DMK | NaOH | Na Stearate | IPA | MEOH | 2P | MIBK |
|---|---|---|---|---|---|---|---|---|---|---|---|---|
| 1 | 2.0 | 80 | 5 | | 6 | 4 | | | | | 5 | |
| 2 | 3.0 | 90 | | 5 | 5 | | 0.2 | | | | | |
| 3 | 10.0 | 85 | 3 | | 3 | 3 | | | | 5 | 1 | |
| 4 | 2.1 | 91 | | 8 | | | | | | | | 1 |
| 5 | 3.1 | 86 | 5 | | | | | 0.2 | 4 | | | 5 |
| 6 | 1.1 | 81 | | | 9 | | 0.5 | 0.5 | | | 9 | |
| 7 | 2.5 | 60 | 4 | 15 | 3 | 3 | | | 6 | 10 | 5 | 4 |
| 8 | 5 | 65 | | 20 | | | | | 10 | | | |
| 9 | 2.4 | 75 | 5 | 4 | | 5 | | | | 6 | | 5 |
| 10 | 4.1 | 80 | 3 | 5 | 2 | 10 | | 0.3 | | | | |
| 11 | 3.2 | 65 | | 5 | 4 | 6 | | | 5 | 4 | 6 | 5 |
| 12 | 5.1 | 96 | | | | | | | | 4 | | |
| 13 | 10.8 | 90 | 5 | | | | | | 5 | | | |
| 14 | 10.0 | 80 | 2 | 6 | 2 | 5 | | | 1 | | 4 | |
| 15 | 1.8 | 80 | | 5 | | | | | | | 15 | |
| 16 | 2.6 | 84 | | | 11 | | | | | | 5 | |
| 1 | 3.3 | 80 | 2 | | | 10 | | | | 2 | | 6 |
| 1 | 12.0 | 90 | | | 7 | | 0.3 | | 3 | | | |
| 1 | 5.4 | 69 | 2 | 20 | 2 | 1 | | | | | 3 | 3 |
| 1 | 6.0 | 91 | | | 4 | | | | | 5 | | |

TABLE B

| Example | Dye Content | Water | PG | DEG | NMP | CET | TBT | TDG | BDL | PHO | 2P | PI2 |
|---|---|---|---|---|---|---|---|---|---|---|---|---|
| 1 | 3.0 | 80 | 15 | | | 0.2 | | | | | 5 | |
| 2 | 9.0 | 90 | | 5 | | | | | | 1.2 | | 5 |
| 3 | 1.5 | 85 | 5 | 5 | | 0.15 | 5.0 | 0.2 | | | | |
| 4 | 2.5 | 90 | | 6 | 4 | | | | | 0.12 | | |
| 5 | 3.1 | 82 | 4 | 8 | | 0.3 | | | | | | 6 |
| 6 | 0.9 | 85 | | 10 | | | | | 5 | 0.2 | | |
| 7 | 8.0 | 90 | | 5 | 5 | | | 0.3 | | | | |
| 8 | 4.0 | 70 | | 10 | 4 | | | | 1 | | 4 | 11 |
| 9 | 2.2 | 75 | 4 | 10 | 3 | | | | 2 | | 6 | |
| 10 | 10.0 | 91 | | | 6 | | | | | | 3 | |
| 11 | 9.0 | 76 | | 9 | 7 | | 3.0 | | | 0.95 | 5 | |
| 12 | 5.0 | 78 | 5 | 11 | | | | | | | 6 | |
| 13 | 5.4 | 86 | | | 7 | | | | | | 7 | |
| 14 | 2.1 | 70 | 5 | 5 | 5 | 0.1 | 0.2 | 0.1 | 5 | 0.1 | 5 | |
| 15 | 2.0 | 90 | | 10 | | | | | | | | |
| 16 | 2 | 88 | | | | | | 10 | | | | |
| 1 | 5 | 78 | | | 5 | | | 12 | | | 5 | |
| 1 | 8 | 70 | 2 | | 8 | | | 15 | | | 5 | |
| 1 | 10 | 80 | | | | | | 8 | | | 12 | |
| 1 | 10 | 80 | | 10 | | | | | | | | |

The invention claimed is:

1. A compound selected from the group consisting of compounds of Formula (2) and salts thereof;

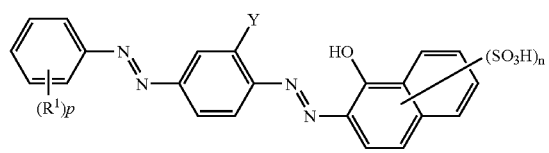

Formula (2)

wherein;

Y and R¹ independently are $CO_2H$, $SO_3H$ or $PO_3H_2$;

p is 1 or 2; and n is 1 to 3.

2. A compound according to claim 1 selected from the group consisting of compounds of Formula (3) and salts thereof;

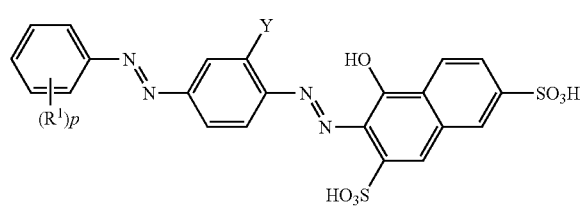

Formula (3)

wherein

Y and R¹ independently are $CO_2H$, $SO_3H$ or $PO_3H_2$; and p is 1 or 2.

3. A compound according to claim 1 selected from the group consisting of compounds of Formula (4) and salts thereof;

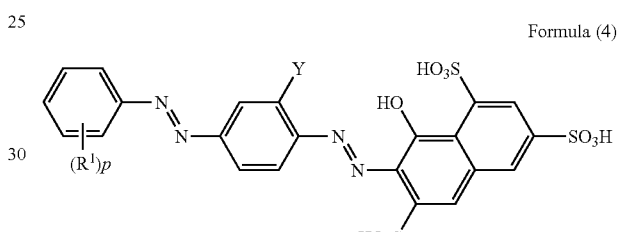

Formula (4)

wherein

Y and R¹ independently are $CO_2H$, $SO_3H$ or $PO_3H_2$; and p is 1 or 2.

4. A compound selected from the group consisting of compounds of Formula (5) and salts thereof;

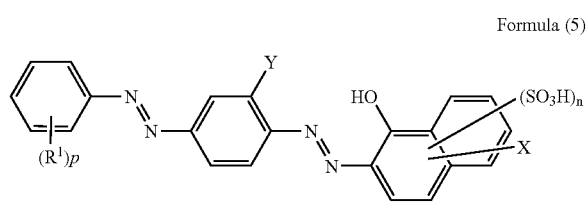

Formula (5)

wherein:

Y and R¹ independently are $CO_2H$, $SO_3H$ or $PO_3H_2$;

X is Cl, Br, F or CN p is 1 or 2; and n is 1 to 3.

5. A compound according to claim 4 selected from the group consisting of compounds of Formula (6) and salts thereof:

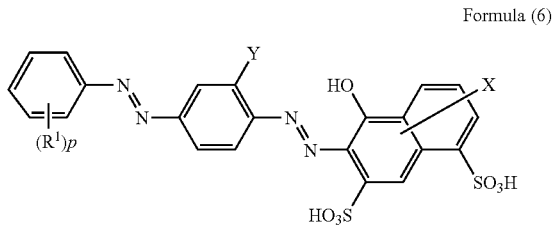

Formula (6)

wherein

Y and R¹ independently are $CO_2H$, $SO_3H$ or $PO_3H_2$;

X is Cl, Br or CN;

p is 1 or 2.

6. A compound according to claim 4 selected from the group consisting of compounds of Formula (7) and salts thereof:

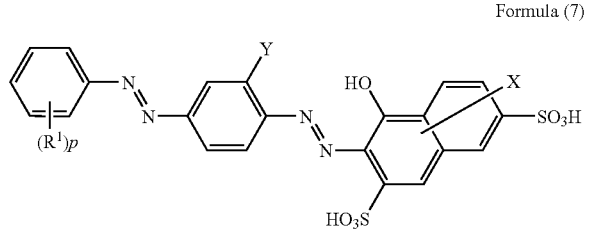

Formula (7)

wherein

Y and R¹ independently are $CO_2H$, $SO_3H$ or $PO_3H_2$;

X is Cl, Br or CN;

p is 1 or 2.

7. A compound selected from the group consisting of compounds of Formula (8) and salts thereof:

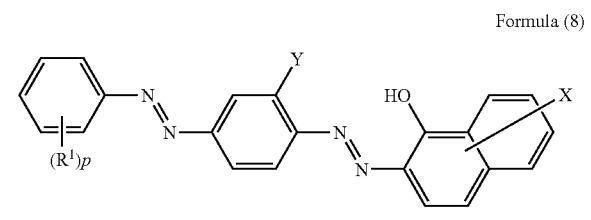

Formula (8)

wherein:

Y and R¹ independently are $CO_2H$, $SO_3H$ or $PO_3H_2$;

X is optionally substituted heterocyclyl; and p is 1 or 2.

8. A compound selected from the group consisting of compounds of Formula (9) and salts thereof:

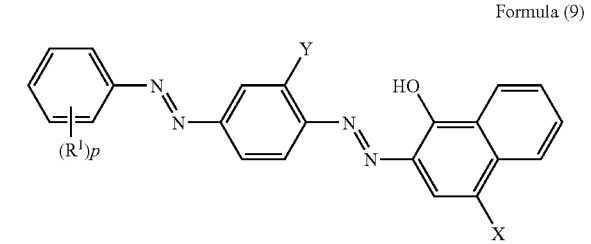

Formula (9)

wherein

N and R¹ independently are $CO_2H$, $SO_3H$ or $PO_3H_2$;

X is optionally substituted triazinyl; and p is 1 or 2.

9. A compound according to claim 8 wherein X is a group of formula:

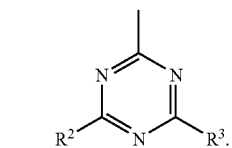

wherein $R^2$ and $R^3$ are substituents.

10. A compound according to claim 9 wherein $R^2$ and $R^3$ are both —OH.

11. A composition comprising a compound as described in claim 1 and a liquid medium.

12. A process for forming an image on a substrate comprising applying thereto a compound selected from the group consisting of compounds of Formula (1) and salts thereof:

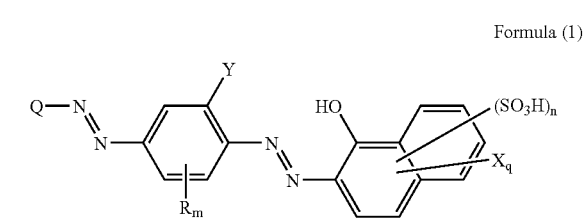

Formula (1)

wherein:

Q is an optionally substituted anti ring;

Y is $CO_2H$, $SO_3H$ or $PO_3H_2$;

R and X are substituents;

n is 0 to 6;

q is 0 to 6; and which is free from fibre reactive groups:

and a liquid medium by means of an ink-jet printer.

13. A substrate printed with a composition according to claim 11.

14. An ink-jet printer cartridge comprising a chamber and an ink wherein the ink is in the chamber and the ink is a composition as described in claim 11.

* * * * *